United States Patent
Trione et al.

(10) Patent No.: US 9,970,041 B2
(45) Date of Patent: May 15, 2018

(54) PROCEDURE FOR THE PRODUCTION OF TIACUMICIN B

(71) Applicant: OLON SPA, Rodano (IT)

(72) Inventors: Guido Trione, Rodano (IT); Antonella Malcangi, Rodano (IT)

(73) Assignee: OLON S.P.A., Rodano, MI (IT)

( * ) Notice: Subject to any disclaimer, the term of this patent is extended or adjusted under 35 U.S.C. 154(b) by 36 days.

(21) Appl. No.: 14/419,955

(22) PCT Filed: Jul. 30, 2013

(86) PCT No.: PCT/EP2013/065994
§ 371 (c)(1),
(2) Date: Feb. 6, 2015

(87) PCT Pub. No.: WO2014/023616
PCT Pub. Date: Feb. 13, 2014

(65) Prior Publication Data
US 2015/0203889 A1 Jul. 23, 2015

(30) Foreign Application Priority Data

Aug. 7, 2012 (IT) .............................. MI2012A1406
May 27, 2013 (IT) .............................. MI2013A0856

(51) Int. Cl.
*C12P 19/58* (2006.01)
*C12P 19/62* (2006.01)
*C07H 17/08* (2006.01)

(52) U.S. Cl.
CPC .............. *C12P 19/58* (2013.01); *C07H 17/08* (2013.01); *C12P 19/62* (2013.01)

(58) Field of Classification Search
None
See application file for complete search history.

(56) References Cited

U.S. PATENT DOCUMENTS

| 4,918,174 A * | 4/1990 | McAlpine .............. C07H 15/10 536/16.8 |
| 2006/0257981 A1* | 11/2006 | Shue ....................... C12N 1/20 435/124 |

FOREIGN PATENT DOCUMENTS

WO    2004014295    2/2004

OTHER PUBLICATIONS

Junker (Foam and Its Mitigation in Fermentation Systems Biotechnology Progress, 2007 23, 767-784.*
Sigma ("Antifoams", Sigma Product Information, St. Louis Missouri, 2005).*
Ivanhoe ("Foam Control Agents", Ivanhoe Industries, available at www.ivanhoeind.com/foam-control-agents/, accessed Jun. 25, 2017).*
Theriault, et al., "Tiacumicins, a novel complex of 18-membered macrolide antibiotics", The Journal of Antibiotics, vol. XL, 1987, pp. 567-574.
Erb, et al., "From natural product to marketed drug: the tiacumicin odyssey", Natural Product Reports, vol. 30, Oct. 30, 2012 pp. 161-174.
International Search Report and Written Opinion of PCT/EP2013/065994, dated Sep. 30, 2013.

* cited by examiner

*Primary Examiner* — Robert J Yamasaki
*Assistant Examiner* — Charles Zoltan Constantine
(74) *Attorney, Agent, or Firm* — Silvia Salvadori, P.C.; Silvia Salvadori

(57) ABSTRACT

The present invention relates to a procedure for the production of tiacumicin B comprising fermentation of a microorganism capable of producing tiacumicin B, in particular of the species *Dactylosporangium aurantiacum* or *Actinoplanes deccanensis*, in a culture broth containing emulsifiers, such as ethoxylated castor oil, in combination with antifoaming products and vegetable oils.

10 Claims, No Drawings

PROCEDURE FOR THE PRODUCTION OF TIACUMICIN B

This application is a U.S. national stage of PCT/EP2013/065994 filed on 30 Jul. 2013, which claims priority to and the benefit of Italian Application No. MI2012A001406 filed on 7 Aug. 2012, and MI2013A000856 filed on 27 May 2013 the contents of which are incorporated herein by reference in their entireties.

FIELD OF INVENTION

The present invention relates to an improved process for the production of tiacumicin B, and in particular to a fermentation method which increases the production of tiacumicin B and prevents its degradation in the culture broth.

PRIOR ART

Tiacumicin B, also known as fidaxomicin, belongs to a family of macrolactones, produced by Actinomycetes, with a complex history.

Tiacumicin B has the same structure as lipiarmycin, which was isolated and described by Lepetit in 1976 in U.S. Pat. No. 3,978,211 as a novel antibiotic produced by cultivating *Actinoplanes deccanensis* A/10655 ATCC21983.

The first patent claimed the product lipiarmycin and a fermentation method for producing it using *Actinoplanes deccanensis* in a nutrient medium containing assimilable sources of carbon, nitrogen and inorganic salts.

In 1986 Abbott Laboratories filed a new patent U.S. Pat. No. 4,918,174 relating to the same product, which in this case was called tiacumicin B, obtained from *Dactylosporangium aurantiacum* subsp. *hamdenensis*.

The producer strain was deposited in the ARS Patent Collection of the Northern Regional Research Center in Peoria, where it was allocated access number NRRL 18085.

The patent claimed the tiacumicins and a process for producing tiacumicins by cultivating *Dactylosporangium aurantiacum* subsp. *hamdenensis* in a nutrient medium.

More recently, Optimer Pharmaceutical filed a new patent U.S. Pat. No. 7,507,564 which discloses an improved process for the production of tiacumicins to obtain a yield exceeding 50 mcg/ml.

The process described by Optimer is still based on fermentation of *Dactylosporangium aurantiacum*, but in a fermentation medium containing an adsorbent resin able to adsorb tiacumicin B.

Tiacumicin B is an RNA polymerase inhibitor.

The great interest in tiacumicin B is due to its biological activity against the multidrug-resistant bacterium (hospital superbug) *Clostridium difficile*.

*C. difficile* is a Gram-positive anaerobic spore-forming bacterium which can cause serious intestinal infections by producing toxins.

Tiacumicin B is a narrow-spectrum antibiotic with good activity against Clostridia and minimal activity towards the rest of the intestinal microflora.

Its specificity can be important in reducing the relapse rate observed with broad-spectrum antibiotics, because maintaining the natural balance of the intestinal bacteria helps provide resistance to recolonisation by pathogens.

It was recently demonstrated that tiacumicin B is effective against the multidrug-resistant Mycobacterium tuberculosis, and also presents good anti-tumoral activity.

DESCRIPTION OF THE INVENTION

The present invention relates to an improved process for the production of tiacumicin B and, particularly, to the use of emulsifiers and/or antifoaming agents, and optionally vegetable oils, during fermentation.

The introduction of said compounds into the culture medium or during fermentation promotes the production of tiacumicin B and protects the molecule from the degradation that occurs naturally during fermentation.

The micro-organism preferably used is *Dactylosporangium aurantiacum*, and in particular *Dactylosporangium aurantiacum* subsp. *Hamdenensis*, or alternatively, *Actinoplanes deccanensis*, and in particular *Actinoplanes deccanensis* A/10655 ATCC21983.

A feedback regulation effect is frequently observed in the biosynthesis of antibiotics, which limits their production potential. In the same way, the low resistance of the producer micro-organism to the synthesised antibiotic can limit the productivity of fermentation.

If the fermentation of tiacumicin B is specifically analysed, it will be seen that as the age of fermentation increases, once peak productivity has been reached, degradation products appear, and the concentration of tiacumicin B declines proportionally.

The fermentation environment is unfavourable to chemically unstable compounds. Variation in pH, accumulation of catabolites and presence of enzyme activity in the aqueous medium are all conditions that contribute to the degradation of unstable compounds.

It has surprisingly been observed that the addition of a mixture consisting of an emulsifier and/or an antifoaming agent, and optionally a vegetable oil, prevents the onset of inhibition and at the same time, preserves the product against degradation.

Tiacumicin B is a liposoluble product that is released into the culture medium during fermentation.

It has surprisingly been observed, by analysing the fermentation broth with HPLC analysis, that the production of tiacumicin B in the medium thus modified continues to increase during fermentation up to 168 h, without the appearance of significant quantities of degradation products.

The object of the present invention is a process for the production of tiacumicin B comprising fermentation of a micro-organism able to produce tiacumicin B, in particular *Dactylosporangium aurantiacum*, and preferably *Dactylosporangium aurantiacum* subsp. *Hamdenensis*, or *Actinoplanes deccanensis*, and preferably *Actinoplanes deccanensis* A/10655 ATCC21983, in a culture broth containing an emulsifier and/or an antifoaming agent, and optionally a vegetable oil.

Emulsifiers consist of a hydrophobic component and a hydrophilic component. Some ethoxylated derivatives of castor oil are used in pharmaceutical formulations for oral, topical or parenteral applications, in the cosmetic field and for animal feed.

Emulsifiers allow stable "oil-in-water" and "water-in-oil" emulsions to be obtained.

The use of an emulsifier promotes the passage of hydrophobic substances into water, forming micelles which present the hydrophilic part to the aqueous environment and internally bind the non-water-soluble substance.

It has surprisingly been observed that the presence of an emulsifier in the fermentation medium aids the production of tiacumicin B, leading to productivity 10 times greater than that obtainable with the basic medium.

The use of an emulsifier, such as the ethoxylated alcohol type (e.g. EMULAN HE50) or the ethoxylated oil type (EMULAN EL, SABOWAX EL40, SABOPAL EL50, ALKAMULS SC/242 and EMULSON CO/36) is particularly useful. The emulsifier is preferably an ethoxylated derivative of castor oil, with a hydrophilic/lipophilic balance of about 14 (HLB 14), such as EMULAN EL, used in concentrations of between 0.5 and 50 g/L, preferably between 5 and 20 g/L.

Similarly, it has been observed that the production of tiacumicin B is increased, though to a more modest extent, by adding an antifoaming agent to the fermentation medium. Antifoaming agents also consist of a hydrophilic component and a hydrophobic component.

The antifoaming agent is preferably a polyether polyol such as Voranol (P2000) or an alkyl-poly-alkoxy-ether such as Clerol DT756. The presence of an antifoaming agent doubles productivity compared with the basic medium. The same result can also be achieved by using an antifoaming agent with a different chemical nature such as poly-alkyl-glycols (e.g. SYNALOX), silicone products (e.g. SAG471) or other antifoaming agents (e.g. AD6800-3F Chimica). The antifoaming agent is added to the medium at a concentration of 0.5-50 g/L, preferably between 5 and 20 g/L.

The use of emulsifiers in the fermenter is limited by the difficulty, under conditions of aeration and stirring of the broth, of controlling the high level of foam it forms.

It has surprisingly been observed that if the emulsifier is used in combination with antifoaming agents, or in combination with antifoaming agents and vegetable oils, problems of high foam formation levels do not arise, and the production of tiacumicin B is further increased.

In particular, the vegetable oil is selected from the group consisting of soybean oil, sunflower oil, olive oil and peanut oil, soybean oil being particularly preferred. The vegetable oil has a concentration in the culture broth of between 0.5 g/L and 100 g/L, preferably between 5 and 20 g/L.

The absence, or at least minimal accumulation, of degradation products produces a higher concentration of tiacumicin B in the broth.

Moreover, as the broth mainly contains tiacumicin B as product, its recovery and purification from the fermentation broth is more efficient.

The presence of a mainly pure product in the broth obviously simplifies the recovery process and eliminates the need for lengthy, expensive purification stages.

The emulsifier and/or antifoaming agent, and optionally vegetable oil, can be present in the culture medium.

Alternatively, the emulsifier and antifoaming agent can be added at the beginning of production of tiacumicin B, either in a single step or gradually during fermentation.

Example 1 (Comparative)

*Dactylosporangium aurantiacum* subsp. *hamdenensis* AB718C-41 NRRL18085 was maintained at −180° C. (WCB). The stock culture was used to inoculate an Erlenmeyer flask (seed flask) containing 40 ml of vegetative medium VPF-1 (Table 1), which was incubated on a rotary stirrer for 48 h at 30° C. and 250-300 rpm.

TABLE 1

| vegetative medium VPF -1 | |
| --- | --- |
| INGREDIENT | 1 L |
| Yeast extract | 7.5 g |
| Dextrose monohydrate | 1 g |

TABLE 1-continued

| vegetative medium VPF -1 | |
| --- | --- |
| INGREDIENT | 1 L |
| Soluble starch | 24 g |
| Soybean peptone | 7.5 g |
| $CaCO_3$ | 4 g | pH corrected to 7.3 with NaOH
Sterilisation 121° C. × 30 min

At the end of incubation, the vegetative culture was transferred aseptically (0.8% of inoculum) to an Erlenmeyer flask (seed flask) containing 30 ml of production medium PF-1 (table 2), which was incubated on a rotary stirrer at 30° C. and 250-300 rpm for 96 h, reaching a productivity level of 50 mcg/ml.

TABLE 2

| production medium PF-1 | |
| --- | --- |
| INGREDIENT | 1 L |
| Dextrose monohydrate | 20 g |
| Starch | 20 g |
| Soybean meal | 10 g |
| Yeast extract | 3 g |
| Soybean oil | 1 g |
| $K_2HPO_4*7H_2O$ | 0.05 g |
| $MgSO_4*7H_2O$ | 0.05 g |
| KCl | 0.03 g |
| $CaCO_3$ | 3 g |

No pH correction
Sterilisation 121° C. × 30 min

Example 2

*Dactylosporangium aurantiacum* subsp. *hamdenensis* AB718C-41 NRRL18085 was maintained at −180° C. (WCB). The stock culture was used to inoculate an Erlenmeyer flask (seed flask) containing 40 ml of vegetative medium VPF-1 (Table 1), which was incubated on a rotary stirrer for 48 h at 30° C. and 250-300 rpm. At the end of incubation, the vegetative culture was transferred aseptically (0.8% of inoculum) to an Erlenmeyer flask (seed flask) containing 30 ml of production medium PF-2 (table 3), which was incubated on a rotary stirrer at 30° C. and 250-300 rpm for 96 h, reaching a productivity level of 125 mcg/ml.

TABLE 3

| production medium PF-2 | |
| --- | --- |
| INGREDIENT | 1 L |
| Dextrose monohydrate | 20 g |
| Starch | 20 g |
| Soybean meal | 10 g |
| Yeast extract | 3 g |
| Soybean oil | 1 g |
| $K_2HPO_4*7H_2O$ | 0.05 g |
| $MgSO_4*7H_2O$ | 0.05 g |
| KCl | 0.03 g |
| $CaCO_3$ | 3 g |
| Clerol DT756 | 5 g |

No pH correction
Sterilisation 121° C. × 30 min

Example 3

*Dactylosporangium aurantiacum* subsp. *hamdenensis* AB718C-41 NRRL18085 was maintained at −180° C. (WCB). The stock culture was used to inoculate an Erlenmeyer flask (seed flask) containing 40 ml of vegetative medium VPF-1 (Table 1), which was incubated on a rotary stirrer for 48 h at 30° C. and 250-300 rpm. At the end of incubation, the vegetative culture was transferred aseptically (0.8% of inoculum) to an Erlenmeyer flask (seed flask) containing 30 ml of production medium PF-3 (table 4), which was incubated on a rotary stirrer at 30° C. and 250-300 rpm for 168 h, reaching a productivity level of 470 mcg/ml.

TABLE 4

| production medium PF-3 | |
|---|---|
| INGREDIENT | 1 L |
| Dextrose monohydrate | 20 g |
| Starch | 40 g |
| Soybean meal | 10 g |
| Yeast extract | 3 g |
| Soybean oil | 1 g |
| $K_2HPO_4*7H_2O$ | 0.05 g |
| $MgSO_4*7H_2O$ | 0.05 g |
| KCl | 0.03 g |
| $CaCO_3$ | 3 g |
| EMULAN EL | 15 g |

No pH correction
Sterilisation 121° C. × 30 min

Example 4

*Dactylosporangium aurantiacum* subsp. *hamdenensis* AB718C-41 NRRL18085 was maintained at −180° C. (WCB). The stock culture was used to inoculate an Erlenmeyer flask (seed flask) containing 40 ml of vegetative medium VPF-1 (Table 1), which was incubated on a rotary stirrer for 48 h at 30° C. and 250-300 rpm. At the end of incubation, the vegetative culture was transferred aseptically (0.8% of inoculum) to an Erlenmeyer flask (seed flask) containing 30 ml of production medium PF-4 (table 5), which was incubated on a rotary stirrer at 30° C. and 250-300 rpm for 168 h, reaching a productivity level of 750 mcg/ml.

TABLE 5

| production medium PF-4 | |
|---|---|
| INGREDIENT | 1 L |
| Dextrose monohydrate | 20 g |
| Starch | 40 g |
| Soybean meal | 10 g |
| Yeast extract | 3 g |
| Soybean oil | 1 g |
| $K_2HPO_4*7H_2O$ | 0.05 g |
| $MgSO_4*7H_2O$ | 0.05 g |
| KCl | 0.03 g |
| $CaCO_3$ | 3 g |
| CLEROL DT756 | 5.5 g |
| EMULAN EL | 5.5 g |

No pH correction
Sterilisation 121° C. × 30 min

Example 5

*Dactylosporangium aurantiacum* subsp. *hamdenensis* AB718C-41 NRRL18085 was maintained at −180° C. (WCB). The stock culture was used to inoculate an Erlenmeyer flask (seed flask) containing 40 ml of vegetative medium VPF-1 (Table 1), which was incubated on a rotary stirrer for 48 h at 30° C. and 250-300 rpm. At the end of incubation, the vegetative culture was transferred aseptically (0.8% of inoculum) to an Erlenmeyer flask (seed flask) containing 30 ml of production medium PF-5 (table 6), which was incubated on a rotary stirrer at 30° C. and 250-300 rpm for 168 h, reaching a productivity level of 730 mcg/ml.

TABLE 6

| production medium PF-5 | |
|---|---|
| INGREDIENT | 1 L |
| Dextrose monohydrate | 20 g |
| Starch | 40 g |
| Soybean meal | 10 g |
| Yeast extract | 3 g |
| Soybean oil | 6.4 g |
| $K_2HPO_4*7H_2O$ | 0.05 g |
| $MgSO_4*7H_2O$ | 0.05 g |
| KCl | 0.03 g |
| $CaCO_3$ | 3 g |
| CLEROL DT756 | 5.5 g |
| EMULAN EL | 5.5 g |

No pH correction
Sterilisation 121° C. × 30 min

Example 6

*Dactylosporangium aurantiacum* subsp. *hamdenensis* AB718C-41 NRRL18085 was maintained at −180° C. (WCB). The stock culture was used to inoculate an Erlenmeyer flask (seed flask) containing 40 ml of vegetative medium VPF-1 (Table 1), which was incubated on a rotary stirrer for 48 h at 30° C. and 250-300 rpm. At the end of incubation, the vegetative culture was transferred aseptically (0.8% of inoculum) to an Erlenmeyer flask (seed flask) containing 30 ml of production medium PF-6 (table 7), which was incubated on a rotary stirrer at 30° C. and 250-300 rpm for 168 h, reaching a productivity level of 880 mcg/ml.

TABLE 7

| production medium PF-6 | |
|---|---|
| INGREDIENT | 1 L |
| Dextrose monohydrate | 20 g |
| Starch | 40 g |
| Soybean meal | 10 g |
| Yeast extract | 3 g |
| Soybean oil | 6.4 g |
| $K_2HPO_4*7H_2O$ | 0.05 g |
| $MgSO_4*7H_2O$ | 0.05 g |
| KCl | 0.03 g |
| $CaCO_3$ | 3 g |
| CLEROL DT756 | 12 g |
| EMULAN EL | 8 g |

No pH correction
Sterilisation 121° C. × 30 min

Example 7

*Dactylosporangium aurantiacum* subsp. *hamdenensis* AB718C-41 NRRL18085 was maintained at −180° C. (WCB). The stock culture was used to inoculate an Erlenmeyer flask (seed flask) containing 40 ml of vegetative medium VPF-1 (Table 1), which was incubated on a rotary stirrer for 48 h at 30° C. and 250-300 rpm. At the end of incubation, the vegetative culture was transferred aseptically (0.8% of inoculum) to an Erlenmeyer flask (seed flask) containing 30 ml of production medium PF-7 (table 8), which was incubated on a rotary stirrer at 30° C. and 250-300 rpm for 168 h, reaching a productivity level of 1090 mcg/ml.

TABLE 8

| production medium PF-7 | |
| --- | --- |
| INGREDIENT | 1 L |
| Dextrose monohydrate | 20 g |
| Starch | 40 g |
| Soybean meal | 10 g |
| Yeast extract | 3 g |
| Soybean oil | 6.4 g |
| $K_2HPO_4*7H_2O$ | 0.05 g |
| $MgSO_4*7H_2O$ | 0.05 g |
| KCl | 0.03 g |
| $CaCO_3$ | 3 g |
| CLEROL DT756 | 12 g |
| ALKAMULS SC/242 | 8 g |

No pH correction
Sterilisation 121° C. × 30 min

Example 8

*Dactylosporangium aurantiacum* subsp. *hamdenensis* AB718C-41 NRRL18085 was maintained at −180° C. (WCB). The stock culture was used to inoculate an Erlenmeyer flask (seed flask) containing 40 ml of vegetative medium VPF-1 (Table 1), which was incubated on a rotary stirrer for 48 h at 30° C. and 250-300 rpm. At the end of incubation, the vegetative culture was transferred aseptically (0.8% of inoculum) to an Erlenmeyer flask (seed flask) containing 30 ml of production medium PF-8 (table 9), which was incubated on a rotary stirrer at 30° C. and 250-300 rpm for 192 h, reaching a productivity level of 1010 mcg/ml.

TABLE 9

| production medium PF-8 | |
| --- | --- |
| INGREDIENT | 1 L |
| Dextrose monohydrate | 20 g |
| Starch | 40 g |
| Soybean meal | 10 g |
| Yeast extract | 3 g |
| Soybean oil | 6.4 g |
| $K_2HPO_4*7H_2O$ | 0.05 g |
| $MgSO_4*7H_2O$ | 0.05 g |
| KCl | 0.03 g |
| $CaCO_3$ | 3 g |
| VORANOL | 15 g |
| EMULAN EL | 8 g |

No pH correction
Sterilisation 121° C. × 30 min

Example 9

*Dactylosporangium aurantiacum* subsp. *hamdenensis* AB718C-41 NRRL18085 was maintained at −180° C. (WCB). The stock culture was used to inoculate an Erlenmeyer flask (seed flask) containing 40 ml of vegetative medium VPF-1 (Table 1), which was incubated on a rotary stirrer for 48 h at 30° C. and 250-300 rpm. At the end of incubation, the vegetative culture was transferred aseptically (0.8% of inoculum) to an Erlenmeyer flask containing 30 ml of production medium PF-1/1 (table 10), which was incubated on a rotary stirrer at 30° C. and 250-300 rpm for 72 h. A solution of EMULAN EL emulsifier and CLEROL DT756 antifoaming agent was added after 72 h to obtain a concentration of 11 g/L for both in the production medium. The fermentation was further incubated up to 168 h, reaching a productivity level of 530 mcg/ml.

TABLE 10

| production medium PF-1/1 | |
| --- | --- |
| INGREDIENT | 1 L |
| Dextrose monohydrate | 20 g |
| Starch | 40 g |
| Soybean meal | 10 g |
| Yeast extract | 3 g |
| Soybean oil | 1 g |
| $K_2HPO_4*7H_2O$ | 0.05 g |
| $MgSO_4*7H_2O$ | 0.05 g |
| KCl | 0.03 g |
| $CaCO_3$ | 3 g |

No pH correction
Sterilisation 121° C. × 30 min

Example 10

*Dactylosporangium aurantiacum* subsp. *hamdenensis* AB718C-41 NRRL18085 was maintained at −180° C. (WCB). The stock culture was used to inoculate 6 Erlenmeyer flasks (seed flasks) containing 40 ml of vegetative medium VPF-1 (Table 1), which were incubated on a rotary stirrer for 48 h at 30° C. and 250-300 rpm. At the end of incubation, the vegetative culture was transferred aseptically (1.4% of inoculum) to a 20 L fermenter containing 16 L of production medium PF-5 (table 6).

The fermentation, conducted at 30° C., with aeration of 0.75 vvm at a counterpressure of 0.5 bar, and stirred at 210-250 rpm, led to productivity of 440 mcg/ml after 120 h fermentation.

Example 11

*Dactylosporangium aurantiacum* subsp. *hamdenensis* AB718C-41 NRRL18085 was maintained at −180° C. (WCB). The stock culture was used to inoculate an Erlenmeyer flask (seed flask) containing 450 ml of vegetative medium VPF-2 (Table 11), which was incubated on a rotary stirrer for 72 h at 30° C. and 150 rpm. At the end of incubation, the vegetative culture was transferred aseptically (1.3% of inoculum) to a 20 L fermenter containing 18 L of production medium PF-9 (table 12).

The fermentation, conducted at 30° C., with aeration of 0.75 vvm at a counterpressure of 0.5 bar, and stirred at 210-250 rpm, led to productivity of 650 mcg/ml after 187 h fermentation.

TABLE 11

| VPF-2 medium | |
| --- | --- |
| INGREDIENT | 1 L |
| Yeast extract | 7.5 g |
| Dextrose monohydrate | 16.5 g |

TABLE 11-continued

| VPF-2 medium | |
|---|---|
| INGREDIENT | 1 L |
| Soybean peptone | 7.5 g |
| $CaCO_3$ | 4 g |
| Voranol | 0.44 g | pH corrected to 7.3 with NaOH
Sterilisation 121° C. × 30 min

TABLE 12

| Medium PF-9 | |
|---|---|
| INGREDIENT | 1 L |
| Dextrose | 20 g |
| Starch | 40 g |
| Soybean meal | 10 g |
| Yeast extract | 3 g |
| Soybean oil | 11 g |
| $K_2HPO_4*7H_2O$ | 0.05 g |
| $MgSO_4*7H_2O$ | 0.05 g |
| KCl | 0.03 g |
| $CaCO_3$ | 3 g |
| CLEROL DT756 | 12 g |
| EMULAN EL | 8 g |

No pH correction
Sterilisation 121° C. × 30 min

Example 12

*Dactylosporangium aurantiacum* subsp. *hamdenensis* AB718C-41 NRRL18085 was maintained at −180° C. (WCB). The stock culture was used to inoculate an Erlenmeyer flask (seed flask) containing 450 ml of vegetative medium VPF-1 (Table 1), which was incubated on a rotary stirrer for 72 h at 30° C. and 120 rpm. At the end of incubation, the vegetative culture was transferred aseptically (1.3% of inoculum) to a 20 L fermenter containing 18 L of production medium PF-10 (table 13).

The fermentation, conducted at 30° C., with aeration of 0.75 vvm at a counterpressure of 0.5 bar, and stirred at 210-250 rpm, led to productivity of 750 mcg/ml after 230 h fermentation.

TABLE 13

| Medium PF-10 | |
|---|---|
| INGREDIENT | 1 L |
| Dextrose | 20 g |
| Starch | 40 g |
| Soybean meal | 10 g |
| Yeast extract | 3 g |
| Soybean oil | 11 g |
| $K_2HPO_4*7H_2O$ | 0.05 g |
| $MgSO_4*7H_2O$ | 0.05 g |
| KCl | 0.03 g |
| $CaCO_3$ | 3 g |
| VORANOL | 15 g |
| EMULAN EL | 8 g |

No pH correction
Sterilisation 121° C. × 30 min

Example 13

A stock culture of *Actinoplanes deccanensis* A/10655 ATCC21983 was used to inoculate an Erlenmeyer flask (seed flask) containing 450 ml of vegetative medium VPF-1 (Table 1), which was incubated on a rotary stirrer for 72 h at 30° C. and 120 rpm.

At the end of incubation, the vegetative culture was transferred aseptically (1.3% of inoculum) to a 20 L fermenter containing 18 L of production medium PF-9 (table 12).

The fermentation, conducted at 30° C., with aeration of 0.75 vvm at a counterpressure of 0.5 bar, and stirred at 210-250 rpm, led to productivity of 800 mcg/ml after 138 h fermentation.

Example 14

A stock culture of *Actinoplanes deccanensis* A/10655 ATCC21983 was used to inoculate an Erlenmeyer flask (seed flask) containing 450 ml of vegetative medium VPF-1 (Table 1), which was incubated on a rotary stirrer for 72 h at 30° C. and 120 rpm. At the end of incubation, the vegetative culture was transferred aseptically (1.3% of inoculum) to a 20 L fermenter containing 18 L of production medium PF-10 (table 13).

The fermentation, conducted at 30° C., with aeration of 0.75 vvm at a counterpressure of 0.5 bar, and stirred at 210-250 rpm, led to productivity of 900 mcg/ml after 143 h fermentation.

The invention claimed is:

1. A process for the preparation of tiacumicin B comprising fermenting a micro-organism so as to produce tiacumicin B in a culture broth containing:

an emulsifier or an emulsified and an anti-foaming agent, and optionally a vegetable oil, wherein the emulsifier is selected from the group consisting of ethoxylated oils and ethoxylated alcohols and said emulsifier has a concentration in the culture broth ranging from 5 g/L to 20 g/L and the anti-foaming agent is selected from the group consisting of polyether polyol or an alkyl-poly-alkoxy-ether and said antifoaming agent has a concentration in the culture broth ranging from 0.5 g/L to 20 g/L.

2. The process according to claim 1 wherein the micro-organism is *Dactylosporangium aurantiacum* or *Actinoplanes deccanensis* or a mutant and/or recombinant strain thereof.

3. The process according to claim 2 wherein the micro-organism is *Dactylosporangium aurantiacum* subsp. *Hamdenensis* or *Actinoplanes deccanensis* A/10655 ATCC21983.

4. The process according to claim 1 wherein the vegetable oil is selected from the group consisting of soybean oil, sunflower oil, olive oil and peanut oil.

5. The process according to claim 4 wherein the vegetable oil is soybean oil.

6. The process according to claim 1 wherein the vegetable oil has a concentration in the culture broth ranging from 0.5 g/L to 100 g/L.

7. The process according to claim 6 wherein the vegetable oil has a concentration in the culture broth ranging from 5 g/L to 20 g/L.

8. The process according to claim 1 wherein the emulsifier or the emulsified and the anti-foaming agent, and optionally the vegetable oil are present in the culture medium before the beginning of production of tiacumicin B.

9. The process according to claim 1 wherein the emulsifier and the anti-foaming agent are added at the beginning of the production of tiacumicin B in one step, or gradually during fermentation.

10. A process for the preparation of tiacumicin B comprising
   fermenting a micro-organism so as to produce tiacumicin B in a culture broth containing an emulsifier, an antifoaming agent and a vegetable oil,
wherein the emulsifier is selected from the group consisting of ethoxylated oils and ethoxylated alcohols, and said emulsifier has a concentration in the culture broth ranging from 5 g/L to 20 g/L and the antifoaming agent is selected from the group consisting of a polyether polyol or an alkyl-polyalkoxy-ether and said antifoaming agent has a concentration in the culture broth ranging from 5 g/L to 20 g/L the and the vegetable oil has a concentration in the culture broth ranging from 0.5 g/L to 100 g/L.

* * * * *